(12) United States Patent
Chang et al.

(10) Patent No.: US 6,573,024 B2
(45) Date of Patent: Jun. 3, 2003

(54) AMMONIUM SALT OF ORGANIC ACID AND RESIST COMPOSITION CONTAINING THE SAME

(75) Inventors: Sheng-Yueh Chang, Taipei Hsien (TW); Jian-Hong Chen, Hsinchu (TW); Ting-Chun Liu, Hsinchu (TW); Tzu-Yu Lin, Hsinchu Hsien (TW); Wen-Yuang Tsai, Taoyuan Hsien (TW)

(73) Assignees: Industrial Technology Research Institute, Hsinchu (TW); Everlight Chemical Industrial Corporation, Taipei (TW)

( * ) Notice: Subject to any disclaimer, the term of this patent is extended or adjusted under 35 U.S.C. 154(b) by 46 days.

(21) Appl. No.: 09/801,742

(22) Filed: Mar. 9, 2001

(65) Prior Publication Data

US 2002/0086234 A1 Jul. 4, 2002

(30) Foreign Application Priority Data

Dec. 28, 2000 (TW) .......................... 89128174 A

(51) Int. Cl.$^7$ .................. G03F 7/004; C07D 295/000; C07C 225/00

(52) U.S. Cl. .................... 430/270.1; 546/184; 564/281; 564/291

(58) Field of Search .................... 430/270.1; 562/2; 546/184; 564/281, 291

(56) References Cited

U.S. PATENT DOCUMENTS 5,958,999 A * 9/1999 Bates et al. ................. 523/161
6,329,121 B2 * 12/2001 Obayashi et al. ........ 430/270.1

OTHER PUBLICATIONS

CA 1992:28583.*
CA 1999:564215.*

* cited by examiner

Primary Examiner—Rosemary Ashton
(74) Attorney, Agent, or Firm—Sughrue Mion, PLLC

(57) ABSTRACT

The present invention provides a novel ammonium salt of an organic acid. When the salt is used as a base additive for a chemically amplified resist, the environmental stability of the resist can be enhanced, and the T-top phenomenon can be effectively prevented. In addition, the line width change caused by acid diffusion can be prevented, and the $E_0$ value of the resist can be decreased.

18 Claims, 3 Drawing Sheets

AMMONIUM SALT OF ORGANIC ACID AND RESIST COMPOSITION CONTAINING THE SAME

BACKGROUND OF THE INVENTION

1. Field of the Invention

The present invention relates to an ammonium salt of an organic acid, and more particularly to a resist composition containing the ammonium salt of organic acid.

2. Description of the Prior Art

A chemically amplified resist is a resist whose degree of dissolution in a developer changes due to the acid generated by exposure. This type of photoresist solution includes a protected resin, a photoacid generator (PAG), and a solvent. The so-called protected resin is a resin that is protected by an acid-labile protective group. The protective group decomposes in the presence of an acid, thus making the resin soluble in an alkali developer.

When the substrate coated with a chemically amplified resist is exposed to light, the photoacid generator will decompose and generate a strong acid, which will catalyze the resin to induce a catalytic hydrolyzation. The protective group (such as an ester group or acetal group) in the resin thus decomposes, making the resin soluble in an alkali developer. In this way, the degree of dissolution of the resist before and after exposure is different, and a pattern can thus be formed.

When the resist is operated in an environment containing a base material, such as hexamethyldisilazane (HMDS) or N-methyl-2-pyrrolidone (NMP), this base material will erode into the surface of the resist. Thus, the acid generated in the exposed area of the resist will be neutralized, which will decrease the concentration of the acid, and the protective groups can not be completely hydrolyzed. The pattern after photolithography thus has adverse phenomenon such as T-top or skin. In addition, the acid generated in the exposed area will diffuse into the unexposed area, thus changing the critical dimension (CD).

To prevent the above problems, either the base concentration in the environment should be strictly controlled, or a base additive is introduced to the resist. In the latter case, the resist as a whole is in basic in nature, which can inhibit the resist from absorbing other base material present in the environment. When the exposure energy is as high as $E_0$ (dose-to-clear energy), a large amount of photoacid will be generated after exposure. A small portion of the photoacid is neutralized by the base additive in the exposed area, while most of the photoacid will catalyze the resin to break the protective groups. Although a small amount of photoacid molecule still goes into the unexposed area through diffusion, the base additive can neutralize the photoacid in the unexposed area. Therefore, the line width change caused by acid diffusion can be prevented.

Since the base additive is introduced mainly for reacting with the photoacid, it is generally called "killer base". Some researchers have used a primary or secondary amine as a killer base, for example, in U.S. Pat. No. 5,942,367. Such a kind of killer base can effectively increase environmental stability of the resist, and the pattern obtained is good. However, the primary or secondary amine will react with some components in the resist composition, such as those containing anhydride or phenol groups. Thus, the storage stability of the resist is decreased. Some researchers have used a tertiary ammonium salt as a killer base, which is disclosed in, for example, U.S. Pat. Nos. 5,633,112 and 5,411,836. However, it is easily seen that the pattern has a slope problem. Also, the rounding problem occurs due to using only one salt.

SUMMARY OF THE INVENTION

Therefore, an object of the present invention is to solve the above-mentioned problems and to provide an ammonium salt of an organic acid. When the salt is used as a base additive for a chemically amplified resist, the environmental stability of the resist can be enhanced, and the T-top phenomenon can be effectively prevented. In addition, the line width change caused by acid diffusion can be prevented, and the $E_0$ value of the resist can be decreased.

To achieve the above objects, the ammonium salt of an organic acid of the present invention has the following formula:

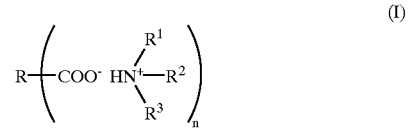
(I)

wherein

R is selected from the group consisting of unsubstituted or substituted cyclic alkyl, cyclic alkenyl, cyclic ester group, and cyclic ketone group having from 3 to 20 carbon atoms, $R^1$, $R^2$, and $R^3$ are selected from the group consisting of H, unsubstituted or substituted linear or branched $C_1$–$C_{20}$ alkyl, $C_3$–$C_{10}$ cyclic alkyl, and unsubstituted or substituted linear or branched $C_1$–$C_{20}$ alkyl containing an N, O, or S atom, when $R^1$, $R^2$, and $R^3$ are unsubstituted or substituted linear or branched $C_1$–$C_{20}$ alkyl, any two of $R^1$, $R^2$, $R^3$ can link together to form a ring, and when $R^1$, $R^2$, and $R^3$ are unsubstituted or substituted linear or branched $C_1$–$C_{20}$ alkyl containing an N, O, or S atom, any two of $R^1$, $R^2$, and $R^3$ can link together to form a ring containing N, O, or S, n is an integer of from 1 to 4, and $R^1$, $R^2$, and $R^3$ are not hydrogen at the same time.

BRIEF DESCRIPTION OF THE DRAWINGS

The present invention will become more fully understood from the detailed description given hereinbelow and the accompanying drawings, given by way of illustration only and thus not intended to be limitative of the present invention.

DETAILED DESCRIPTION OF THE INVENTION

Figure 1:
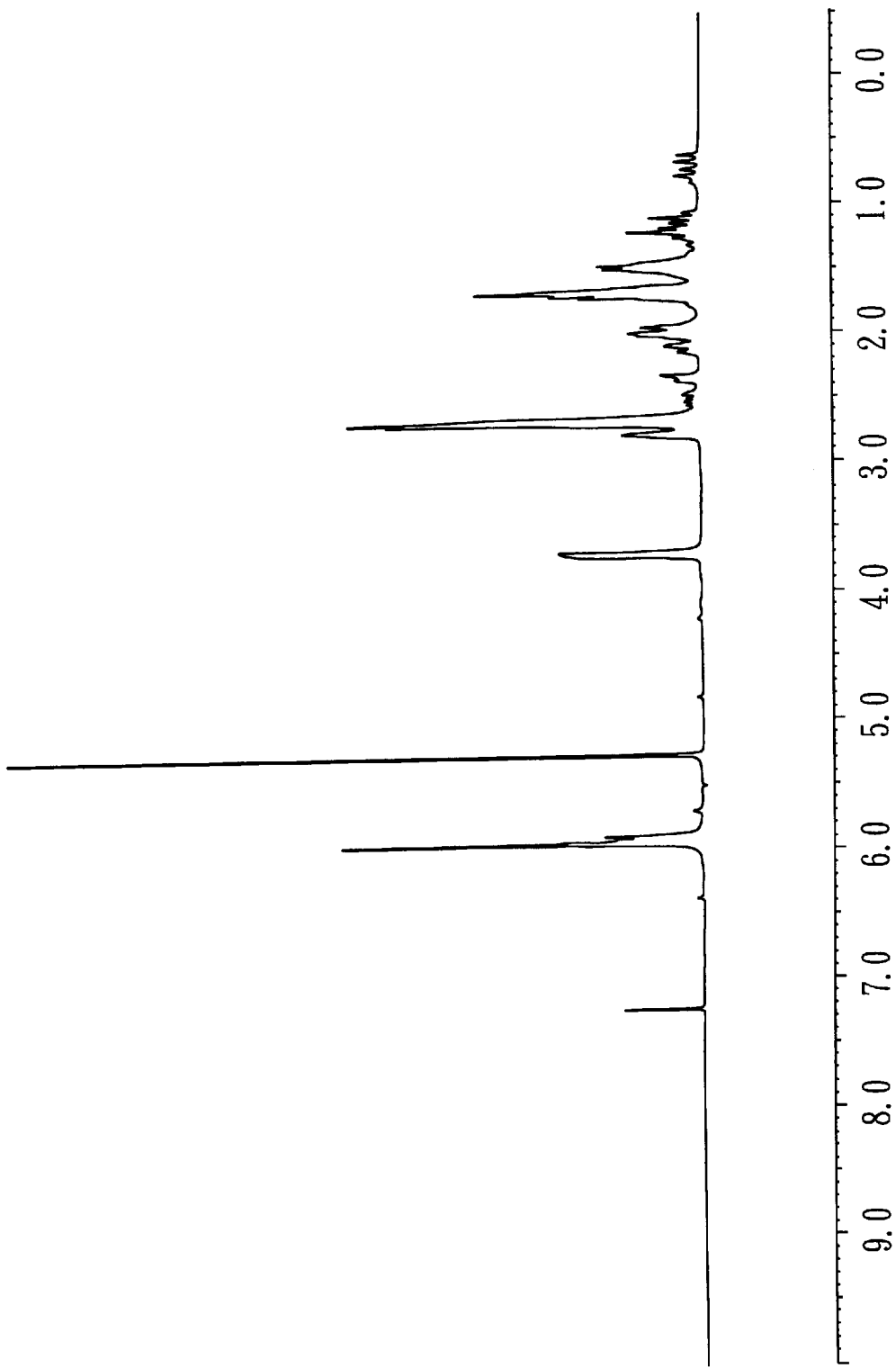
FIG. 1 is the NMR spectrum of the ammonium salt of organic acid (A) obtained from Example 1 of the present invention.

The substituent on R, $R^1$, $R^2$, and $R^3$ of the ammonium salt of organic acid represented by formula (I) of the present invention can be carboxy, hydroxy, halogen, sulfonyl, ester group, ketone group, ether group, or sulfide group.

In formula (I), when R is unsubstituted or substituted cyclic alkyl or cyclic alkenyl, representative examples include:

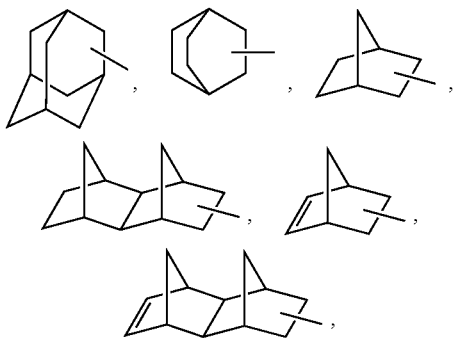

and $C_6H_{14}$—.

In the ammonium salt of organic acid of the present invention, representative examples of the ammonium salt portion

include:

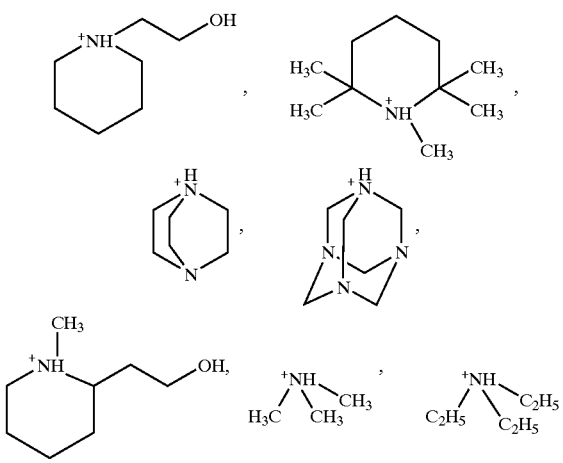

The method for preparing the ammonium salt of organic acid of the present invention is simple. That is, the ammonium salt of organic acid of the present invention can be obtained by reacting a suitable organic acid and a suitable amine in a suitable solvent. Suitable organic acid can be represented by the formula R—COOH, wherein R is defined as above. Representative examples of organic acids include

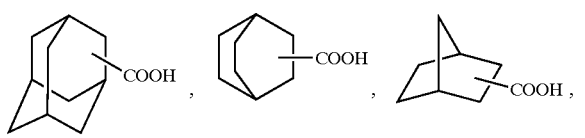

-continued

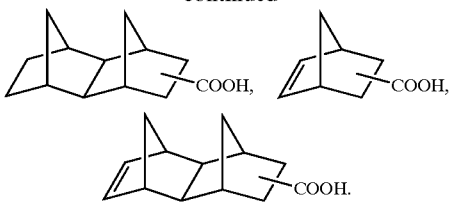

R on the organic acid R—COOH can have other substituents. When the substituent on R is one or more than one carboxy group (—COOH), the organic acid thus has two or more than two carboxy groups. Each carboxy group on the organic acid can react with the amine. Representative examples of such organic acids having more than one carboxy group include:

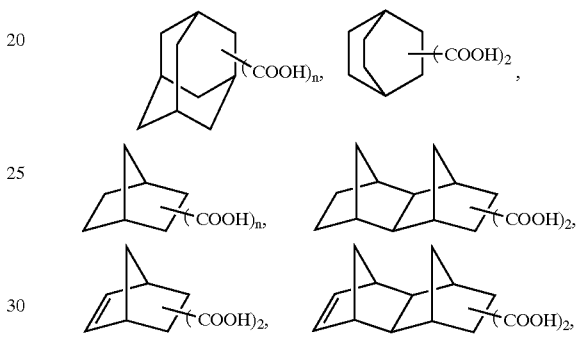

wherein n is an integer of from 2 to 4.

The amine suitable for use in the present invention has the following formula:

wherein $R^1$, $R^2$, and $R^3$ are defined as above.

Representative examples of amines suitable for use in preparing the ammonium salt of organic acid of the present invention include:

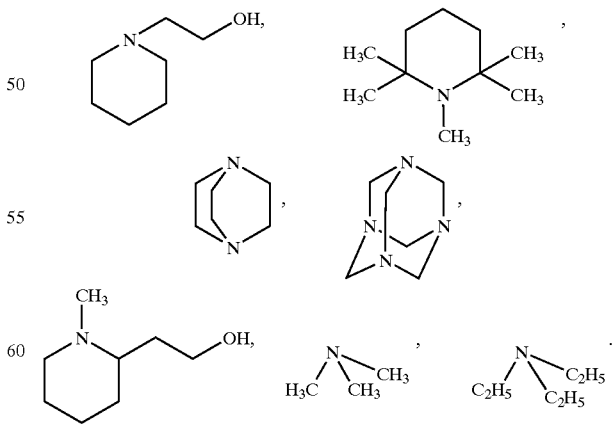

In order to make the ammonium salt of organic acid of the present invention to be used as a base additive for a resist, particularly a chemically amplified resist, preferably, the ammonium salt of organic acid is dissolved in an organic solvent, and has a decomposition temperature higher than 100° C.

According to the present invention, the resist composition containing the ammonium salt of organic acid includes the following components:
- (a) the ammonium salt of organic acid of the present invention represented by formula (I);
- (b) a resin having an acid-labile protective group, wherein the protective group decomposes in the presence of an acid such that the resin becomes alkaline soluble; and
- (c) a photoacid generator in an amount of 1–20 wt % of the resin (b), wherein the ammonium salt of organic acid (a) is present in an amount of 1–20 mole % of the photoacid generator (c).

The resist composition of the present invention can further include component (d) an amine. The amine is optional and not a necessary component. The total amount of components (a) and (d) is 1–20 mole % of component (c). The weight ratios of the amine and the ammonium salt of organic acid are X:Y, wherein $0 \leq X \leq 0.95$, $0 < Y \leq 1$, $X+Y=1$.

Representative examples of the amines (d) include

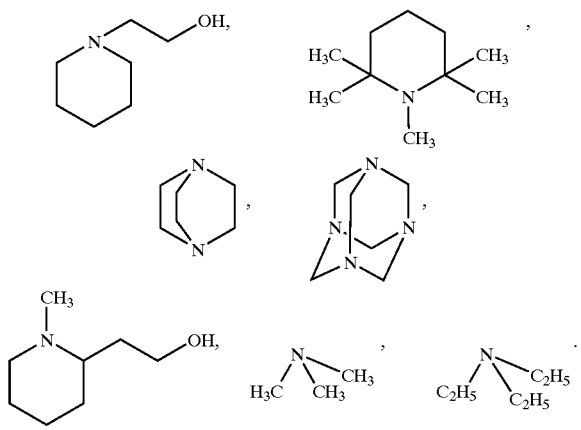

According to the present invention, suitable resin can be any resin generally used for resists, particularly a resin used for a chemically amplified resist. The acid-labile protective group of the resin can be t-butoxy, t-butoxycarbonyloxy (t-BOC), or t-butoxycarbonylmethyl. Suitable resin can be generally a polyhydroxystyrene, in which the hydroxy is substituted with the protective group. A representative example is poly-t-butoxycarbonyloxystyrene.

The photoacid generator suitable for use in the present invention can be sulfonium salts, iodonium salts, onium salts, or sulfonates. Representative examples include:

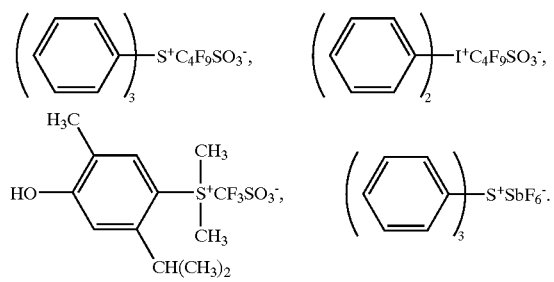

The resist composition of the present invention is photosensitive at a wavelength of 150 nm to 600 nm, preferably at a wavelength of 157 nm, 193 nm or 248 nm.

The following examples are intended to illustrate the process and the advantages of the present invention more fully without limiting its scope, since numerous modifications and variations will be apparent to those skilled in the art.

Preparation of Ammonium Salts of Organic Acid (A)–(C)

EXAMPLE 1

2.04 g of dinorbornene carboxylic acid was dissolved in 15 ml of dichloromethane. After complete dissolution, 3.1 g of 1,2,2,6,6-pentamethyl piperidine was added dropwise to the solution. The mixture was stirred for 3 hours. After the reaction was complete, the mixture was concentrated under reduced pressure to give a liquid product, which was then dried with a vacuum pump to give a pale brown liquid. The liquid was recrystallized with hexane to produce a white powder, which was finally dried with a vacuum pump to produce a white powder. It was confirmed by the NMR spectrum (FIG. 1) that an ammonium salt of an organic acid (A) was successfully prepared.

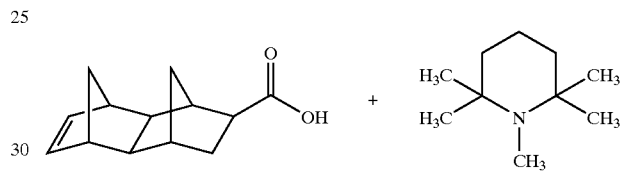

EXAMPLE 2

Figure 2:
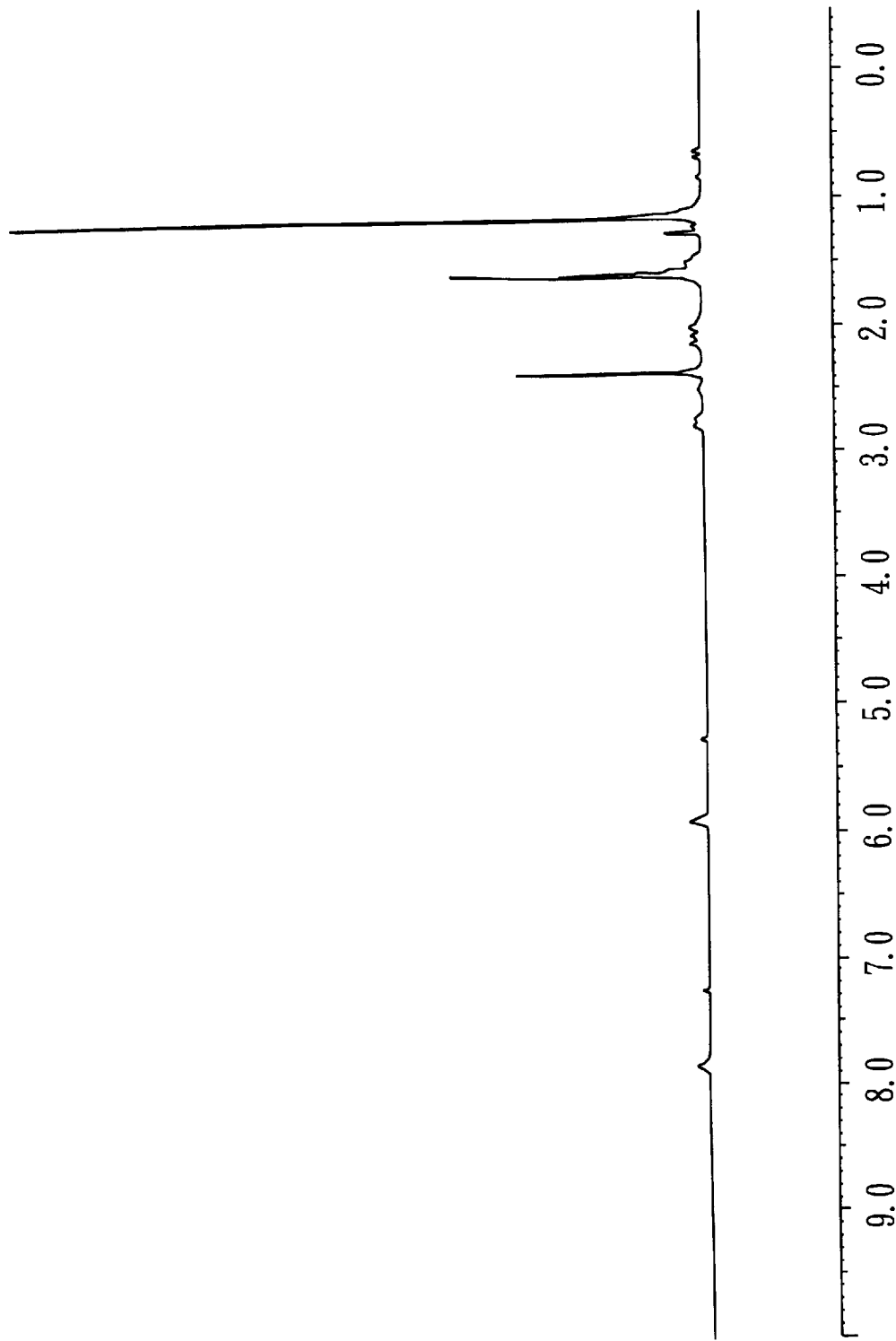
FIG. 2 is the NMR spectrum of the ammonium salt of organic acid (B) obtained from Example 2 of the present invention.

2.04 g of dinorbornene carboxylic acid was dissolved in 15 ml of dichloromethane. After complete dissolution, 2.58 g of [1-(2-hydroxyethyl)piperidine] was added dropwise to the solution. The mixture was stirred for 3 hours. After the reaction was complete, the mixture was concentrated under reduced pressure to give a liquid product, which was then dried with a vacuum pump to give a pale brown liquid. The liquid was recrystallized with hexane, and finally dried with a vacuum pump to produce a pale brown sticky liquid. It was confirmed by the NMR spectrum (FIG. 2) that an ammonium salt of an organic acid (B) was successfully prepared.

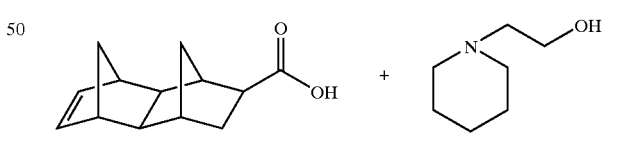

EXAMPLE 3

Figure 3:
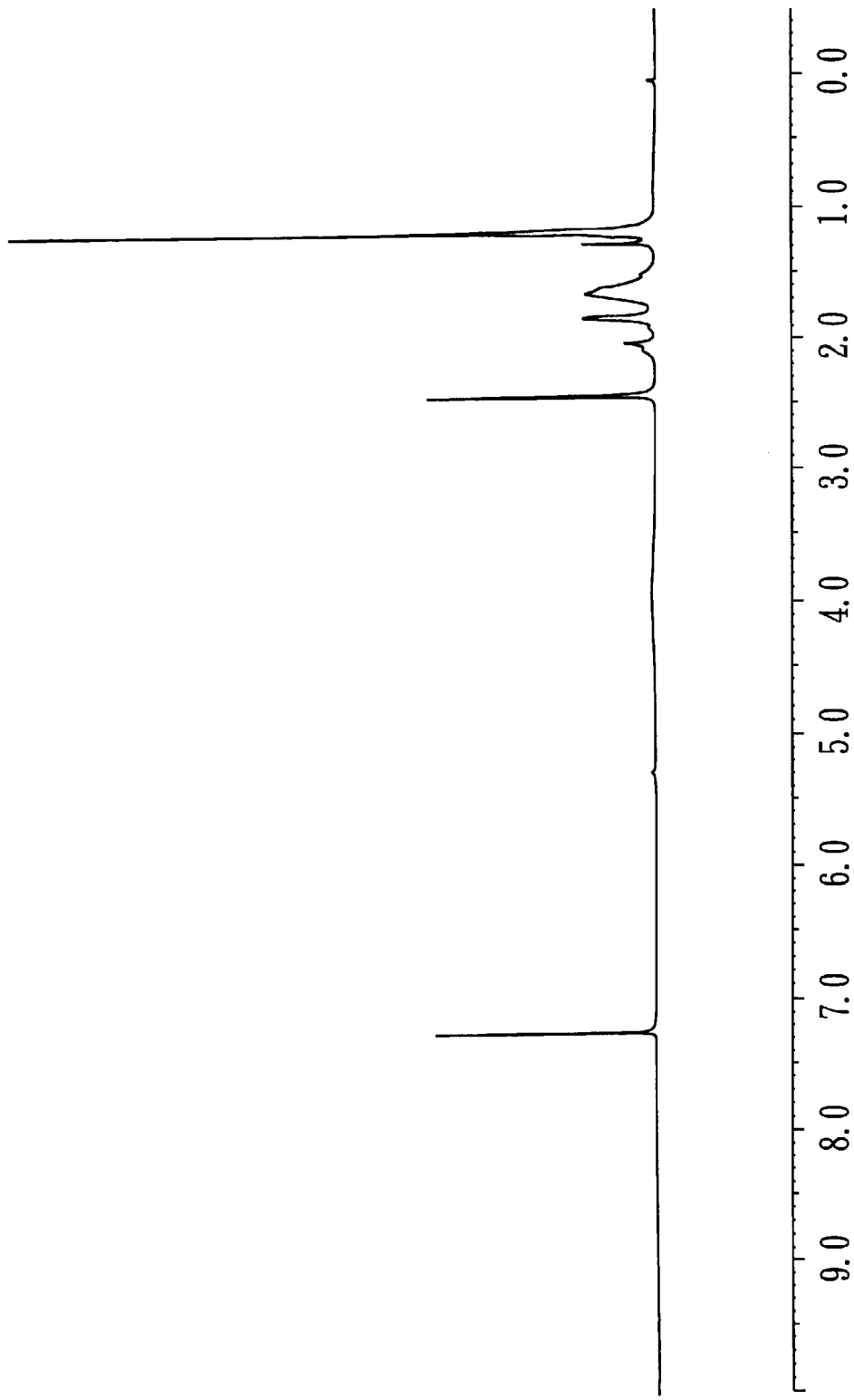
FIG. 3 is the NMR spectrum of the ammonium salt of organic acid (C) obtained from Example 3 of the present invention.

2.22 g of 1,3-adamantane dicarboxylic acid was dissolved in 15 ml of dichloromethane. After complete dissolution, 3.1 g of 1,2,2,6,6-pentamethyl piperidine was added dropwise to the solution. The mixture was stirred for 3 hours. After the reaction was complete, the mixture was concentrated under reduced pressure to give a liquid product, which was then dried with a vacuum pump. It was confirmed by using the NMR spectrum (FIG. 3) that an ammonium salt of an organic acid (C) was successfully prepared.

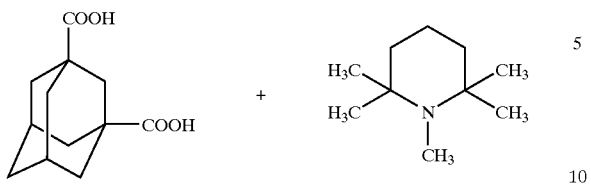

Preparation and Evaluation of Resist Composition

EXAMPLE 4

2 g of a copolymer of t-butyl dinorbornene carboxylate, maleic anhydride, 2-methyl-2-norbornyl-acrylate, and 2-methyl-norbornyl-norbornene carboxylate (molar ratio= 0.1:0.2:0.2:0.1), 0.06 g of triphenylsulfonium nonafluorosulfate (PAG; photoacid generator), and 0.06 g of t-butyl cholate (dissolution rate inhibitor) were dissolved in 9.15 g of propylene glycol methyl ether acetate (PGMEA) and stirred thoroughly. 1.15 g of the ammonium salt of organic acid (C) obtained from Example 3 (as a killer base) (0.1 wt % in PGMEA) was added to the mixture to obtain a resist composition.

The resist composition was filtered through a 0.4 μm filter. The filtrate was applied to an 8 inch wafer by spin coating at 3000 rpm and soft baked at 140° C. for 90 seconds. The coated wafer was exposed through a mask using 193 nm laser and then baked at 140° C. for 90 seconds. The wafer was then developed, rinsed, and dried to form a resist pattern. The dose-to-clear energy ($E_0$) was 3.90 mJ/cm$^2$, and the contrast value was 15.38.

COMPARATIVE EXAMPLE

The same procedures were employed as described in Example 4, except that the killer base was replaced by 1.33 g of 1-(2-hydroxyethyl)piperidine (0.1 wt % in PGMEA). The coated wafer was exposed, baked, and developed to form a resist pattern. The dose-to-clear energy ($E_0$) was 15.5 mJ/cm$^2$.

The foregoing description of the preferred embodiments of this invention has been presented for purposes of illustration and description. Obvious modifications or variations are possible in light of the above teaching. The embodiments chosen and described provide an excellent illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. An ammonium salt of an organic acid, having the following formula:

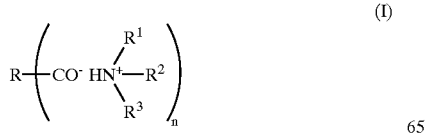

(I)

wherein
R is selected from the group consisting of unsubstituted or substituted cyclic alkyl, cyclic alkenyl, cyclic ester group, and cyclic ketone group having from 3 to 20 carbon atoms, $R^1$, $R^2$, and $R^3$ are selected from the group consisting of H, unsubstituted or substituted linear or branched $C_1$–$C_{20}$ alkyl, $C_3$–$C_{10}$ cyclic alkyl, and unsubstituted or substituted linear or branched $C_1$–$C_{20}$ alkyl containing an N, O, or S atom, when $R^1$, $R^2$, and $R^3$ are unsubstituted or substituted linear or branched $C_1$–$C_{20}$ alkyl, any two of $R^1$, $R^2$, $R^3$ can link together to form a ring, and when $R^1$, $R^2$, and $R^3$ are unsubstituted or substituted linear or branched $C_1$–$C_{20}$ alkyl containing an N, O, or S atom, any two of $R^1$, $R^2$, and $R^3$ can link together to form a ring containing N, O, or S, n is an integer of from 1 to 4, $R^1$, $R^2$, and $R^3$ are not hydrogen at the same time, and at least one of R, $R^1$, $R^2$ and $R^3$ is substituted and the substituent is selected from the group consisting of carboxy, hydroxy, halogen, sulfonyl, ester group, ketone group, ether group, and sulfide group.

2. The ammonium salt of an organic acid as claimed in claim 1, wherein R is substituted and the substituent on R is carboxy.

3. The ammonium salt of an organic acid as claimed in claim 1, wherein R is unsubstituted or substituted cyclic alkyl or cyclic alkenyl having from 3 to 20 carbon atoms.

4. The ammonium salt of an organic acid as claimed in claim 3, wherein R is selected from the group consisting of

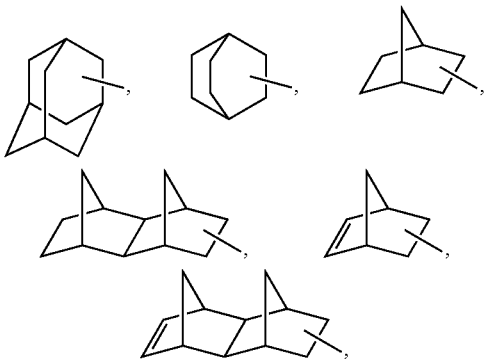

and $C_6H_{14}$—.

5. The ammonium salt of an organic acid as claimed in claim 4, wherein R is

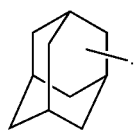

6. The ammonium salt of an organic acid as claimed in claim 4, wherein R is

7. The ammonium salt of an organic acid as claimed in claim 1, wherein the ammonium salt portion

is selected from the group consisting of

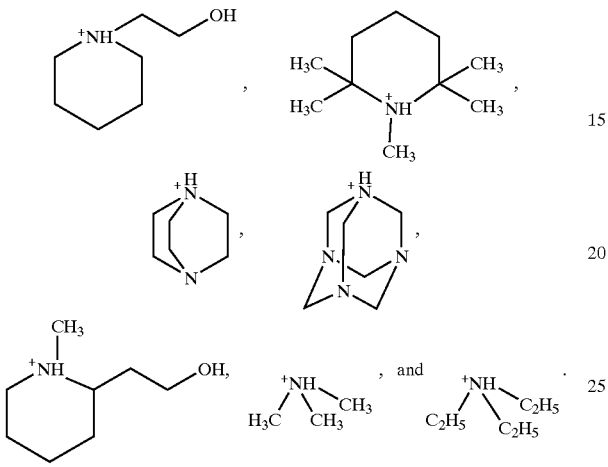

8. The ammonium salt of an organic acid as claimed in claim 7, wherein the ammonium salt portion is

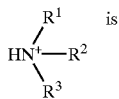

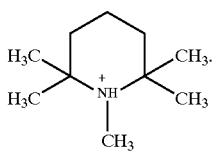

9. The ammonium salt of an organic acid as claimed in claim 7, wherein the ammonium salt portion is

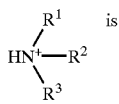

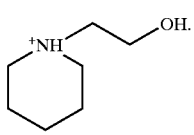

10. The ammonium salt of an organic acid as claimed in claim 1, wherein the salt can be dissolved in an organic solvent.

11. The ammonium salt of an organic acid as claimed in claim 1, wherein the salt has a decomposition temperature higher than 100° C.

12. A resist composition, comprising the following components:

(a) an ammonium salt of an organic acid, having the following formula:

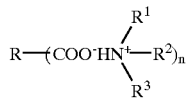

(I)

wherein

R is selected from the group consisting of unsubstituted or substituted cyclic alkyl, cyclic alkenyl, cyclic ester group, and cyclic ketone group having from 3 to 20 carbon atoms, $R^1$, $R^2$, and $R^3$ are selected from the group consisting of H, unsubstituted or substituted linear or branched $C_1$–$C_{20}$ alkyl, $C_3$–$C_{10}$ cyclic alkyl, and unsubstituted or substituted linear or branched $C_1$–$C_{20}$ alkyl containing an N, O, or S atom, when $R^1$, $R^2$, and $R^3$ are unsubstituted or substituted linear or branched $C_1$–$C_{20}$ alkyl, any two of $R^1$, $R^2$, $R^3$ can link together to form a ring, and when $R^1$, $R^2$, and $R^3$ are unsubstituted or substituted linear or branched $C_1$–$C_{20}$ alkyl containing an N, O, or S atom, any two of $R^1$, $R^2$, and $R^3$ can link together to form a ring containing N, O, or S, n is an integer of from 1 to 4, and $R^1$, $R^2$, and $R^3$ are not hydrogen at the same time;

(b) a resin having an acid-labile protective group, wherein the protective group decomposes in the presence of an acid such that the resin becomes alkaline soluble; and (c) a photoacid generator present in an amount of 1–20 wt % of the resin (b), wherein the ammonium salt of organic acid (a) is present in an amount of 1–20 mole % of the photoacid generator (c).

13. The resist composition as claimed in claim 12, further comprising (d) an amine, wherein the weight ratios of the amine and the ammonium salt of organic acid are X:Y, wherein $0 \leq X \leq 0.95$, $0 < Y \leq 1$, X+Y=1, and the total amount of components (a) and (d) is 1–20 mole % of component (c).

14. The resist composition as claimed in claim 13, wherein the amine is selected from the group consisting of

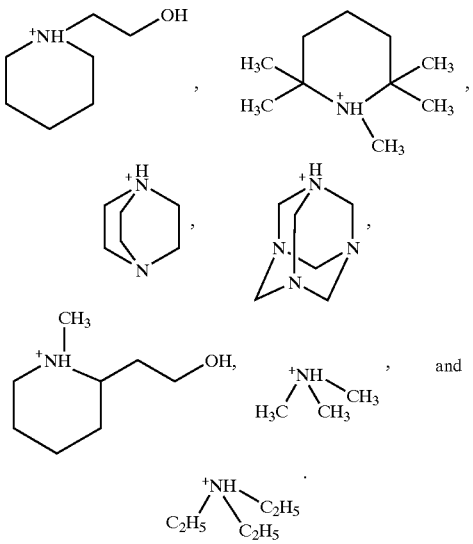

15. The resist composition as claimed in claim 12, wherein the acid-labile protective group of the resin is selected from the group consisting of t-butoxy, t-butoxycarbonyloxy (t-BOC), and t-butoxycarbonylmethyl.

16. The resist composition as claimed in claim 12, wherein the photoacid generator is selected from the group consisting of sulfonium salts, iodonium salts, onium salts, and sulfonates.

17. The resist composition as claimed in claim 12, wherein the composition is photosensitive at a wavelength of from 150 nm to 600 nm.

18. The resist composition as claimed in claim 12, wherein the composition is photosensitive at wavelengths of 157 nm, 193 nm or 248 nm.

* * * * *